United States Patent [19]

Mallion

[11] 4,021,425
[45] May 3, 1977

[54] PROCESS FOR PRODUCING ENONE INTERMEDIATES

[75] Inventor: Keith Blakeney Mallion, Macclesfield, England

[73] Assignee: Imperial Chemical Industries Limited, London, England

[22] Filed: Nov. 13, 1975

[21] Appl. No.: 631,606

[30] Foreign Application Priority Data

Dec. 12, 1974 United Kingdom ............ 53757/74

[52] U.S. Cl. ........................................... 260/240 R
[51] Int. Cl.² ..................................... C07D 307/77
[58] Field of Search ..................... 260/343.3, 240 R

[56] References Cited

FOREIGN PATENTS OR APPLICATIONS

| | | | |
|---|---|---|---|
| 2,401,763 | 7/1974 | Germany | 260/343.3 |
| 7,306,462 | 11/1973 | Netherlands | 260/343.3 |
| 1,350,971 | 4/1974 | United Kingdom | 260/343.3 R |

*Primary Examiner*—Anton H. Sutto
*Attorney, Agent, or Firm*—Cushman, Darby & Cushman

[57] ABSTRACT

The disclosure relates to a novel four-stage reaction sequence whereby known enone intermediates for prostaglandin analogues may be obtained from 4β-dimethoxymethyl-2,3,3αβ,6αβ-tetrahydro-5α-hydroxy-6β-iodo-2-oxocyclopenteno[b]furan in substantially increased yield. A novel intermediate produced in the novel four-stage reaction sequence is also claimed.

6 Claims, No Drawings

PROCESS FOR PRODUCING ENONE INTERMEDIATES

This invention relates to a process which is useful in the manufacture of prostaglandins and prostaglandin-like compounds, and more particularly it relates to an improved process for the manufacture of known prostaglandin intermediates.

The improved process is especially useful in the manufacture of known 16-aryloxy-17,18,19,20-tetranor-prostaglandin analogues of the E- and F-series, but it will be appreciated that a similar improved process may be applied to the synthesis of a great variety of other known prostaglandins and prostaglandin analogues.

In a published synthesis of 16-aryloxy-17,18,19,20-tetranor-prostaglandin analogues of the E- and F-series (see, for example, West German Offenlegungsschrift No. 2,223,365), a key enone intermediate V is synthesised by a four stage process from the known dimethylacetal I by reaction thereof with 4-phenylbenzoyl chloride to give the ester II which is treated with tributyl tin hydride to produce the deiodinated dimethylacetal III. The deiodinated dimethylacetal III is hydrolysed to the aldehyde IV, which is then reacted with a phosphonate of the formula $(CH_3O)_2PO.CH_2CO.CH_2OR^1$, wherein $R^1$ is a phenyl or naphthyl radical, optionally substituted, in the presence of a strong base, to give the key enone intermediate V. This four stage process is shown in the following reaction scheme:

We have now found, and herein lies our invention, that a re-ordering of the four reactions involved in manufacturing V from I results in an unexpected and most valuable increased yield. For example, in the case where $R^1$ stands for a 3-chlorophenyl radical, the published procedure will manufacture V from I in an overall yield of about 29%, whereas the improved process of the present invention will manufacture V from I in an overall yield of up to about 47%, thus enabling about 72% (47−29/29 = 18/29 = 62%) more of the key enone intermediate V to be obtained from a given quantity of the dimethylacetal I. We have also found that if, in our modified process, the benzoate enone corresponding to the 4-phenylbenzoate enone V is used, a further increase in yield may be obtained. In fact, the benzoate enone corresponding to V may be obtained in an overall yield of up to about 56% from I, and may be used in the same way as the phenylbenzoate V in the synthesis of 16-aryloxy-17,18,19,20-tetranor-prostaglandin analogues of the E- and F-series referred to above.

Thus, according to the invention, there is provided a process for the manufacture of an enone of the formula:

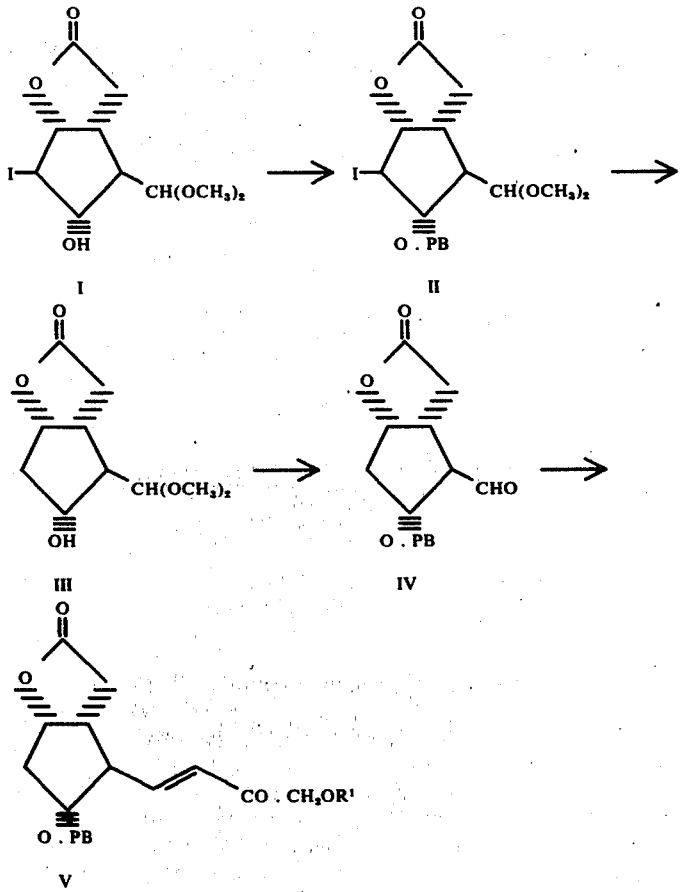

PB = 4-phenylbenzoyl

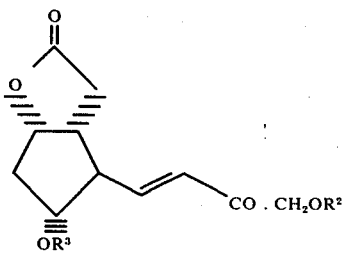

wherein $R^2$ is a phenyl or naphthyl radical which is unsubstituted or bears one or more substituents selected from halogen atoms, hydroxy or phenyl radicals, alkyl, alkenyl, halogenoalkyl or alkoxy radicals each of 1 to 4 carbon atoms or dialkylamino radicals wherein each alkyl is of 1 to 4 carbon atoms, and $R^3$ is a benzoyl or 4-phenylbenzoyl radical, which comprises the following four successive stages:

1. the reduction of 4β-dimethoxymethyl-2,3,3aβ, 6aβ-tetrahydro-5α-hydroxy-6β-iodo-2-oxocyclopenteno [b]-furan, (I), for example with a complex metal hydride such as tri-n-butyl tin hydride, to give 4β-dimethoxymethyl-2,3,3aβ, 6aβ-tetrahydro-5α-hydroxy-2-oxocyclopenteno[b]furan;

2. the hydrolysis of the product from stage (1), for example in a two-phase system comprising a mineral acid such as hydrochloric acid and a water-immiscible organic solvent such as toluene or a mixture of toluene and petroleum ether, to give 2,3,3aβ, 6aβ-tetrahydro-5α-hydroxy-2-oxocyclopenteno [b]-furan-4β-carbaldehyde;

3. the reaction of the product from stage (2) with a phosphonate of the formula $(R^5O)_2PO.CH_2COCH_2OR^2$, wherein $R^2$ has the meaning stated above and $R^4$ is an alkyl radical of 1 to 6 carbon atoms, for example a methyl radical, in the presence of a base, for example potassium carbonate or sodium hydroxide, to give an enone of the formula:

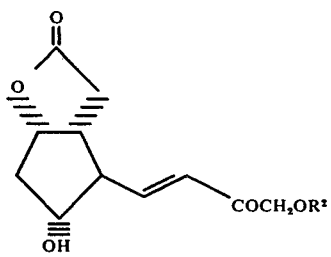

wherein $R^2$ has the meaning stated above;

4. the acylation of the product VII from stage (3) with a reactive derivative of benzoic acid or 4-phenylbenzoic acid, for example benzoyl chloride or 4-phenylbenzoyl chloride.

It is to be understood that the products obtained in stages (1), (2) and (3) need not be isolated and purified but may be used, as obtained, in the next subsequent stage.

Preferred enones of the formula VI which may be manufactured in higher yield that hitherto by the process of the invention are 4β-[4-(3-chlorophenoxy)-3-oxobut-1-trans-enyl]-2,3,3aβ, 6aβ-tetrahydro-2-oxo-5α-(4-phenyl-benzoyloxy)cyclopenteno[b]furan, 2,3,3aβ, 6aβ-tetrahydro-2-oxo-4β-[3-oxo-4-(3-trifluoromethylphenoxy)but-1-trans-enyl]-5α-(4-phenylbenzoyloxy)cyclopenteno[b]furan, 5α-benzoyloxy-4β-[4-(3-chlorophenoxy-3-oxobut-1-trans-enyl]-2,3,3aβ, 6aβ- -tetrahydro-2-oxocyclopenteno[b]furan and 5α-benzoyloxy-2,3,3aβ, 6aβ-tetrahydro-2-oxo-4β-[3-oxo-4-(3-trifluoromethylphenoxy)but-1-trans-enyl]cyclopenteno [b]furan.

The enones of the formula VII obtained as the product of stage (3) are novel compounds, and are provided as a further feature of the invention.

Particular novel enones of the invention of the formula VII are 4β-[4-(3-chlorophenoxy)-3-oxobut-1-trans-enyl]-2,3,3aβ, 6aβ-tetrahydro-5α-hydroxy-2-oxocyclopenteno [b]furan and 2,3,3aβ, 6aβ-tetrahydro-5α-hydroxy-2-oxo-4β-[3-oxo-4-(3-trifluoromethylphenoxy)but-1-trans-enyl]-cyclopenteno[b]furan. These enones are additionally useful as substrates, or intermediates to substrates, for steroselective reduction to lead to the prostaglandin analogues cloprostenol and fluprostenol.

According to a further feature of the invention there is provided a process for the manufacture of an enone of the formula VII, which comprises stage (3) as described above.

The invention is illustrated, but not limited, by the following Example:

EXAMPLE 1

STAGE (1)

4β-Dimethoxymethyl-2,3,3aβ, 6aβ-tetrahydro-5α-hydroxy-6β-iodo-2-oxocyclopenteno [b]furan (8.0 g.) and tri-n-butyl tin oxide (13.2 g.) were dissolved in toluene (60 ml.) by warming, under an atmosphere of argon. Polymethylhydrogen siloxan (2.56 ml.) was added, followed by benzoyl peroxide (400 mg.), and the mixture was stirred and warmed to 80° C. for 2½ hours, adding, after the first hour, a further portion (400 mg.) of benzoyl peroxide. The solution of 4β-dimethoxymethyl-2,3,3aβ, 6aβ-tetrahydro-5α-hydroxy-2-oxocyclopenteno [b]-furan thus obtained was cooled and used in stage (2).

STAGE (2)

The toluene solution obtained as the product from stage (1) was stirred, diluted with petroleum ether (b.p. 40°-60° C., 60 ml.) and shaken with 0.5N hydrochloric acid (30 ml.). The mixture was filtered through "Hyflo" (trade mark) kieselguhr and the aqueous acid layer was separated. The filter pad was washed with 0.5N hydrochloric acid (30 ml.) and this washing was used to re-extract the toluene solution. The aqueous acid layer was separated and combined with the first extract, using 0.5N hydrochloric acid (4 ml.) as a wash solvent in the transfers. The combined acid extracts were washed with a mixture (30 ml.) of equal parts of petroleum ether (b.p. 40°-60° C.) and toluene, and then allowed to stand overnight, by which time all of the acetal was hydrolysed, giving a solution of the aldehyde, 2,3,3aβ, 6aβ-tetrahydro-5α-hydroxy-2-oxocyclopenteno[b]furan-4β-carbaldehyde in dilute hydrochloric acid.

STAGE (3)

The solution of aldehyde obtained as the product from stage (2) was stirred, cooled in an ice-bath, and neutralised by the addition of portions of solid potassium carbonate (approximately 1.2 g.). The neutral solution was then added over 20 minutes to a vigorously stirred mixture of dimethyl [3-(3-chlorophenoxy)-2-oxopropyl]-phosphonate (9.66 g.) and potassium carbonate (4.56 g.) in tetrahydrofuran (40 ml.) and water (10 ml.) and maintained at 5° to 7° C. by cooling in an ice-bath. The mixture was stirred for 1¼ hours, glyoxylic acid (5.4 g.) and potassium carbonate (13.6 g.) were then added, and the mixture was stirred for a further 15 minutes to convert any excess of the phosphonate reagent to a water soluble derivative. The mixture was then extracted with ethyl acetate (2 × 50 ml.), the extracts were combined, washed with 1:1 saturated brine: water and dried, and the solvent was evaporated to give 4β-[4-(3-chlorophenoxy)-3-oxobut-1-trans-enyl]-2,3,3aβ, 6aβ-tetrahydro-5α-hydroxy-2-oxycyclopenteno [b]furan as a gum (approximately 7.6 g.) which may be used directly in stage (4), or crystallised from 15% ethyl acetate in ether to give the crystalline product, m.p. 103°–104° C.

STAGE (4)

The crude product from stage (3), (7.6 g.) was dissolved in dry toluene (30 ml.) and pyridine (8.4 ml.), and the solution was stirred under argon while 4-phenyl-benzoyl chloride (7.06 g.) was added. After 1 hour, the solution was diluted with ethyl acetate (50 ml.) and washed with 2N hydrochloric acid (1 × 50, 2 × 25 ml.), saturated sodium bicarbonate solution (50 ml.) and brine (25 ml.). The organic solution was dried over magnesium sulphate and filtered, and the solvents were evaporated to give 4β-[4-(3-chlorophenoxy)-3-oxobut-1-trans-enyl]-2,3,3aβ, 6aβ-tetrahydro-2-oxo-5α-(4-phenylbenzoyloxy)cyclopenteno[b]-furan as a gum, which on trituration with a mixture of equal parts of methanol and ether gave a solid product which was filtered off and washed with ether (5.60 g., 46.8% overall yield for the four stages), $R_F = 0.7$ approximately (thin layer chromatography on silica gel developed with 15% isopropanol in toluene).

EXAMPLE 2

The process described in Example 1 was repeated, except that in stage (4), an equivalent quantity of benzoyl chloride was used in place of 4-phenylbenzoyl chloride to give 5α-benzoyloxy-4β-[4-(3-chlorophenoxy)-3-oxobut-1-trans-enyl]-2,3,3aβ, 6aβ-tetrahydro-2-oxocyclopenteno [b]furan in 56% overall yield for the four stages, $R_F = 0.7$ approximately (thin layer chromatography on silica gel developed with 15% isopropanol in toluene). The n.m.r. spectrum in deuteriochloroform showed the following characteristic signals (δ values):

| | |
|---|---|
| 2.2 – 3.2, 6H, multiplet, | —CH$_2$—and > CH— of cyclopentenofuran rings. |
| 4.64, 2H, singlet, | —CH$_2$O— |
| 4.8 – 5.4, 2H, multiplet, | 2 <> CH . O— |
| 6.47, 1H, doublet, | —CH:CH . CO— |
| 6.65 – 8.1, 10H, multiplet, | —CH:CH . CO—and aromatic protons. |

EXAMPLE 3

The process described in Example 1 was repeated with the following modifications:

a. in stage (1), the argon atmosphere and the two additions of benzoyl peroxide were omitted;

b. the reaction mixture in stage (3) was treated as described in Example 1 as far as the washing with 1:1 saturated brine: water. The aqueous layer was separated and discarded, and the organic layer was concentrated by evaporating the solvent at about 50° C./250 mm. Hg. pressure until the volume was reduced to about 40 ml. Toluene (80 ml.) was added, and the distillation was continued until the volume was reduced to about 50 ml. and the boiling point reached about 60°–65° C. The warm solution of 4β-[4-(3-chlorophenoxy)-3-oxobut-1-trans-enyl]-2,3,3aβ, 6aβ-tetrahydro-5α-hydroxy-2-oxocyclopenteno[b]furan in dry toluene, containing 5–10% of ethyl acetate so obtained was cooled, treated with pyridine (8.4 ml.) and then with 4-phenylbenzoyl chloride, as described in stage (4) of Example 1.

Alternatively, the product of stage (3) was isolated by allowing the warm, concentrated solution, obtained as described above, to cool and stand for some time, whereupon the product crystallised and was filtered off, washed with ether and crystallised from ethyl acetate/ether, m.p. 103°–104° C.

EXAMPLE 4

The process described in Example 1 was repeated, using an equivalent amount of dimethyl [2-oxo-3-(3-trifluoromethylphenoxy)propyl]phosphonate in place of the dimethyl [3-(3-chlorophenoxy)-2-oxopropyl]-phosphonate, to give 2,3,3aβ, 6aβ-tetrahydro-2-oxo-4β-[3-oxo-4-(3-trifluromethylphenoxy)but-1-trans-enyl]-5α-(4-phenylbenzoyloxy)cyclopenteno[b]furan, m.p. 125°–127° C., $R_F = 0.7$ (silica gel, developed in 20% ethyl acetate in methylene dichloride). The yield over the four stages was approximately 50%, compared with approximately 25% for the prior art process.

What I claim is:

1. A process for the manufacture of an econe of the formula:

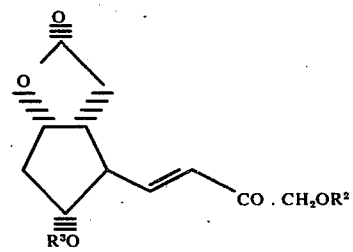

wherein $R^2$ is phenyl or naphthyl which is unsubstituted or bears one or more substituents selected from halogen, hydroxy, phenyl, alkyl, alkenyl, halogenoalkyl or alkoxy each of 1 to 4 carbon atoms or dialkylamino wherein each alkyl is of 1 to 4 carbon atoms, and $R^3$ is benzoyl or 4-phenylbenzoyl, which comprises the following four successive stages:

1. the reduction with a complex metal hydride of 4β-dimethoxymethyl-2,3,3aβ,6aβ-tetrahydro-5α-hydroxy-6β-iodo-2-oxocyclopenteno[b ]-furan to give 4β-dimethoxymethyl-2,3,3aβ,6aβ-tetrahydro-5α-hydroxy-2-oxocyclopenteno[b]furan;

2. the hydrolysis in a two-phase system comprising a mineral acid and a water-immiscible organic solvent of the product from stage (1) to give 2,3,3aβ,-6aβ-tetrahydro-5α-hydroxy-2-oxocyclopenteno[b]-furan-4β-carbaldehyde;

3. the reaction of the product from stage (2) with a phosphonate of the formula $(R_4O)_2PO.CH_2COCH_2OR^2$, wherein $R^2$ has the meaning stated above and $R^4$ is alkyl of 1 to 6 carbon atoms, in the presence of a base, to give an enone of the formula:

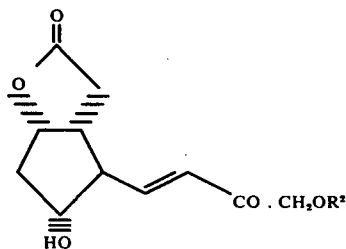

4. the acylation of the product from stage (3) with a reactive derivative of benzoic acid or 4-phenylbenzoic acid.

2. A process as claimed in claim 1 wherein the complex metal hydride is tri-n-butyl tin hydride.

3. A process as claimed in claim 1 wherein the mineral acid is hydrochloric acid and the water-immiscible organic solvent is toluene or a mixture of toluene and petroleum ether.

4. A process as claimed in claim 1 wherein in stage (3) the base is potassium carbonate or sodium hydroxide.

5. A process as claimed in claim 1 wherein in stage (4) the reactive derivative of benzoic acid or 4-phenylbenzoic acid is benzoyl chloride or 4-phenylbenzoyl chloride.

6. A process as claimed in claim 1 for the manufacture of 4β-[4-(3-chlorophenoxy)-3-oxobut-1-trans-enyl]-2,3,3aβ,6aβ-tetrahydro-2-oxo-5α-(4-phenylbenzoyloxy)-cyclopenteno[b]furan, 2,3,3aβ,6aβ-tetrahydro-2-oxo-4β-[3-oxo-4-(3-trifluoromethylphenoxy)-but-1-trans-enyl]-5 0 -(4-phenylbenzoyloxy)cyclopenteno[b]furan, 5α-benzoyloxy-4β-[4-(3-chlorophenoxy)-3-oxobut-1-trans-enyl]-2,3,3aβ,6aβ-tetrahydro-2-oxocyclopenteno[b]furan or 5α-benzoyloxy-2,3,3aβ,6aβ-tetrahydro-2-oxo-4β-[3-oxo-4-(3-trifluoro-methylphenoxy)but-1-trans-enyl]cyclopenteno[b]furan.

* * * * *